US012229916B2

(12) United States Patent
Yin et al.

(10) Patent No.: US 12,229,916 B2
(45) Date of Patent: Feb. 18, 2025

(54) SUPER-RESOLUTION RECONSTRUCTION METHOD AND APPARATUS FOR THREE-DIMENSIONAL CONTRAST-ENHANCED ULTRASOUND IMAGES

(71) Applicant: Nanjing Leapsonics Technology Co., Ltd., Nanjing (CN)

(72) Inventors: Jingyi Yin, Nanjing (CN); Jue Zhang, Nanjing (CN)

(73) Assignee: Nanjing Leapsonics Technology Co., Ltd., Nanjing (CN)

( * ) Notice: Subject to any disclaimer, the term of this patent is extended or adjusted under 35 U.S.C. 154(b) by 410 days.

(21) Appl. No.: 17/838,059

(22) Filed: Jun. 10, 2022

(65) Prior Publication Data

US 2022/0309613 A1    Sep. 29, 2022

Related U.S. Application Data

(63) Continuation of application No. PCT/CN2021/093469, filed on May 13, 2021.

(30) Foreign Application Priority Data

May 18, 2020    (CN) .......................... 202010419606.4

(51) Int. Cl.
*G06T 3/4053*    (2024.01)
*A61B 8/00*    (2006.01)
(Continued)

(52) U.S. Cl.
CPC ............ *G06T 3/4053* (2013.01); *A61B 8/481* (2013.01); *G06T 5/30* (2013.01); *G06T 5/70* (2024.01);
(Continued)

(58) Field of Classification Search
CPC ........... G06T 3/4053; G06T 5/30; G06T 5/70; G06T 2207/10136; A61B 8/481
See application file for complete search history.

(56) References Cited

U.S. PATENT DOCUMENTS

| 11,748,849 B2* | 9/2023 | Song .................... G06T 3/4007 |
| 2015/0196279 A1* | 7/2015 | Ketterling .............. A61B 8/145 |
| | | 600/447 |

(Continued)

FOREIGN PATENT DOCUMENTS

| CN | 107361791 A | 11/2017 |
| CN | 108324324 A * | 7/2018 |

(Continued)

OTHER PUBLICATIONS

International Search Report issued in corresponding PCT Application No. PCT/CN2021/093469, dated Aug. 13, 2021.

(Continued)

*Primary Examiner* — Ted W Barnes
(74) *Attorney, Agent, or Firm* — Westbridge IP LLC

(57) ABSTRACT

Disclosed are a super-resolution reconstruction method and an apparatus for three-dimensional contrast-enhanced ultrasound images, a computer readable storage medium and an electronic device. The method includes: performing at least one thinning operation on a first three-dimensional local image sequence, the thinning operation being configured to enhance motion trajectories of microbubbles; and performing an image reconstruction operation based on the first three-dimensional local image sequence subjected to the at least one thinning operation, so as to generate three-dimensional super-resolution images. The super-resolution reconstruction method for the three-dimensional contrast-enhanced ultrasound images, by means of performing thinning operations (for example, respectively performing a first thinning operation and a second thinning operation) on the (Continued)

first three-dimensional local image sequence, highlights motion trajectories of microbubbles, thereby improving a signal-to-noise ratio of an image. Compared with a prior method, the reconstruction efficiency and precision of the three-dimensional super-resolution imaging are improved.

18 Claims, 9 Drawing Sheets

(51) Int. Cl.
*G06T 5/30* (2006.01)
*G06T 5/70* (2024.01)
*G06T 7/136* (2017.01)
*G06T 7/30* (2017.01)
*G06T 7/50* (2017.01)
*G06T 7/68* (2017.01)

(52) U.S. Cl.
CPC ............... *G06T 7/136* (2017.01); *G06T 7/30* (2017.01); *G06T 7/50* (2017.01); *G06T 7/68* (2017.01); *G06T 2207/10016* (2013.01); *G06T 2207/10136* (2013.01); *G06T 2207/30004* (2013.01)

(56) References Cited

U.S. PATENT DOCUMENTS

2018/0144472 A1* 5/2018 Kullberg ............ G01R 33/4828
2020/0178939 A1* 6/2020 Song ..................... A61B 8/5223
2020/0229792 A1* 7/2020 Moshavegh ........ G01S 7/52039
2022/0296216 A1* 9/2022 Yin ...................... A61B 8/5223

FOREIGN PATENT DOCUMENTS

| CN | 108836392 A | * | 11/2018 | ............... A61B 8/06 |
| CN | 110772285 A | * | 2/2020 | ............... A61B 8/06 |
| CN | 111588409 A | | 8/2020 | |
| CN | 107361791 B | * | 10/2020 | ............... A61B 8/06 |
| CN | 112435305 A | * | 3/2021 | |
| CN | 113260314 A | * | 8/2021 | ............ A61B 8/085 |
| WO | 2018222724 A1 | | 12/2018 | |
| WO | WO-2018222724 A1 | * | 12/2018 | ............... A61B 8/06 |

OTHER PUBLICATIONS

Ackermann et al., Detection and Tracking of Multiple Microbubbles in Ultrasound B-Mode Images, IEEE Transactions on Ultrasonics, Ferroelectrics, and Frequency Control, vol. 63, No. 1, pp. 72-82, dated Jan. 2, 2016.

Extended European Search Report issued in counterpart European Patent Application No. 21809726.9, dated Jan. 5, 2023.

Solun et al., Super-resolution Ultrasound Localiation Microscopy through Deep Learning, Arxiv. org, Cornell University Library, XP081431922, dated Apr. 20, 2018.

* cited by examiner

SUPER-RESOLUTION RECONSTRUCTION METHOD AND APPARATUS FOR THREE-DIMENSIONAL CONTRAST-ENHANCED ULTRASOUND IMAGES

CROSS-REFERENCE TO RELATED APPLICATIONS

The present application is a continuation of International Application No. PCT/CN2021/093469, filed on May 13, 2021, which claims priority to Chinese Patent Application No. 202010419606.4, filed on May 18, 2020. All applications are incorporated herein by reference in their entireties.

TECHNICAL FIELD

The present application relates to the field of image processing technologies, in particular to a super-resolution reconstruction method and an apparatus for three-dimensional contrast-enhanced ultrasound images, a computer readable storage medium and an electronic device.

BACKGROUND

Ultrasound Localization Microscopy (ULM) mainly achieves a purpose of microvascular imaging by locating isolated microbubble contrast agents in microvessels, and importance of it is self-evident. Compared with the prior art, ULM improves a spatial resolution by about ten times, and realizes three-dimensional ultrasound super-resolution imaging of complicated microvasculature in three-dimensional space.

However, the prior three-dimensional ultrasound super-resolution imaging methods based on ULM not only require a long-time acquisition of three-dimensional contrast-enhanced ultrasound images, but also are susceptible to noise interference, which in turn leads to a decrease in localization precision of microbubbles, so it is difficult to achieve the theoretical spatial resolution of ULM with low signal-to-noise ratio contrast-enhanced ultrasound images collected in a short period of time in clinic.

SUMMARY

In order to solve the above technical problems, a super-resolution reconstruction method and an apparatus for three-dimensional contrast-enhanced ultrasound images, a computer readable storage medium and an electronic device are provided according to embodiments of the present application.

According to an aspect, an embodiment of the present application provides a super-resolution reconstruction method for three-dimensional contrast-enhanced ultrasound images, applied to a first three-dimensional local image sequence including microbubbles. The super-resolution reconstruction method for three-dimensional contrast-enhanced ultrasound images includes: performing at least one thinning operation on the first three-dimensional local image sequence, the thinning operation being used to enhance motion trajectories of microbubbles; and performing an image reconstruction operation based on the first three-dimensional local image sequence subjected to the at least one thinning operation, so as to generate a three-dimensional super-resolution image.

According to an embodiment of the present application, the performing at least one thinning operation on the first three-dimensional local image sequence includes: performing a first thinning operation on the first three-dimensional local image sequence to generate a second three-dimensional local image sequence corresponding to the first three-dimensional local image sequence, the first thinning operation being used to enhance motion trajectories of microbubbles for a first time; and performing a second thinning operation on the second three-dimensional local image sequence to generate a third three-dimensional local image sequence corresponding to the second three-dimensional local image sequence, the second thinning operation being used to enhance motion trajectories of microbubbles for a second time. The performing an image reconstruction operation based on the first three-dimensional local image sequence subjected to the at least one thinning operation, so as to generate a three-dimensional super-resolution image includes: performing an image reconstruction operation based on the third three-dimensional local image sequence, so as to generate a three-dimensional super-resolution image corresponding to the third three-dimensional local image sequence.

According to an embodiment of the present application, the performing a first thinning operation on the first three-dimensional local image sequence to generate a second three-dimensional local image sequence corresponding to the first three-dimensional local image sequence includes: determining, for each frame of the first three-dimensional local images in the first three-dimensional local image sequence, distance information between a microbubble area in the first three-dimensional local image and a background area corresponding to the microbubble area; performing a first weighting operation on the first three-dimensional local images based on the distance information to generate first weighted images; and generating the second three-dimensional local image sequence based on the first weighted images respectively corresponding to the first three-dimensional local images in the first three-dimensional local image sequence.

According to an embodiment of the present application, the determining distance information between a microbubble area in the first three-dimensional local image and a background area corresponding to the microbubble area includes: performing binarization processing on the first three-dimensional local images based on the microbubble area and the background area to generate a binarized image; and determining the distance information between the microbubble area and the background area based on the binarized image.

According to an embodiment of the present application, the multiple second three-dimensional local images included in the second three-dimensional local image sequence are obtained by performing the first thinning operation on the multiple first three-dimensional local images in the first three-dimensional local image sequence frame by frame.

According to an embodiment of the present application, a pixel value of a pixel coordinate corresponding to the microbubble area is set to 1, and a pixel value of a pixel coordinate corresponding to the background area is set to 0.

According to an embodiment of the present application, the microbubble area includes a plurality of pixel blocks. The determining distance information between a microbubble area in the first three-dimensional local image and a background area corresponding to the microbubble area includes: determining a shortest distance from each pixel block in the plurality of pixel blocks to the background area respectively; and determining the distance information based on the shortest distances respectively corresponding to the plurality of pixel blocks.

According to an embodiment of the present application, the performing a second thinning operation on the second three-dimensional local image sequence to generate a third three-dimensional local image sequence corresponding to the second three-dimensional local image sequence includes: performing, for each second three-dimensional local image in the second three-dimensional local image sequence, a degree of radial symmetry estimation operation on each pixel unit in the second three-dimensional local image, so as to determine a weight value corresponding to the pixel unit; performing a second weighting operation on the second three-dimensional local image based on the weight values respectively corresponding to the pixel units in the second three-dimensional local image to generate a second weighted image; and generating a third three-dimensional local image sequence based on the second weighted images respectively corresponding to the second three-dimensional local images in the second three-dimensional local image sequence.

According to an embodiment of the present application, the degree of radial symmetry estimation operation is implemented based on a degree of radial symmetry calculation method in super-resolution radial fluctuations.

According to an embodiment of the present application, a number of sampling points is 12 and a sampling radius is 1 in the degree of radial symmetry estimation operation.

According to an embodiment of the present application, before the performing at least one thinning operation on the first three-dimensional local image sequence, the method further includes: performing a registration operation on the first three-dimensional local image sequence. The registration operation includes a rigid registration operation and/or a flexible registration operation.

According to an embodiment of the present application, the performing a registration operation on the first three-dimensional local image sequence includes: performing, by using three-dimensional Morphon multi-scale registration method, the registration operation on the first three-dimensional local image sequence.

According to an embodiment of the present application, the performing an image reconstruction operation based on the first three-dimensional local image sequence subjected to the at least one thinning operation, so as to generate a three-dimensional super-resolution image includes: performing an accumulation operation on the third three-dimensional local images of the third three-dimensional local image sequence based on image sequence information corresponding to the first three-dimensional local image sequence, so as to generate the three-dimensional super-resolution image.

According to another aspect, an embodiment of the present application provides a super-resolution reconstruction apparatus for three-dimensional contrast-enhanced ultrasound images, applied to a first three-dimensional local image sequence including microbubbles. The super-resolution reconstruction apparatus for three-dimensional contrast-enhanced ultrasound images includes: a thinning module and a reconstruction module signally connected to the thinning module. The thinning module is configured to perform at least one thinning operation on the first three-dimensional local image sequence. The thinning operation is configured to enhance motion trajectories of microbubbles. The reconstruction module is configured to perform an image reconstruction operation based on the first three-dimensional local image sequence subjected to the at least one thinning operation, so as to generate a three-dimensional super-resolution image.

According to another aspect, the super-resolution reconstruction apparatus for three-dimensional contrast-enhanced ultrasound images further includes a registration module signally connected to the thinning module. The registration module is configured to perform a registration operation on the first three-dimensional local image sequence. The registration operation includes rigid registration operations and/or flexible registration operations.

According to another aspect, an embodiment of the present application provides a computer readable storage medium storing a computer program for executing the super-resolution reconstruction method for three-dimensional contrast-enhanced ultrasound images according to any one of the above embodiments.

According to another aspect, an embodiment of the present application provides an electronic device, including: a processor; and a memory for storing executable instructions of the processor. The processor is configured to execute the super-resolution reconstruction method for three-dimensional contrast-enhanced ultrasound images according to any one of the above embodiments.

In the super-resolution reconstruction method for three-dimensional contrast-enhanced ultrasound images according to embodiments of the present application, by means of performing thinning operations (for example, respectively performing a first thinning operation and a second thinning operation) on the first three-dimensional local image sequence, motion trajectories of microbubbles are highlighted, thereby improving a signal-to-noise ratio of an image. Compared with a prior super-resolution reconstruction method for the three-dimensional contrast-enhanced ultrasound images, embodiments of the present application may greatly improve a reconstruction efficiency and reconstruction precision of the three-dimensional super-resolution image reconstruction operation.

DETAILED DESCRIPTION OF THE EMBODIMENTS

The technical schemes in embodiments of the present application will be described clearly and completely below with reference to the accompanying drawings in the embodiments of the present application. Obviously, the described embodiments are only a part of the embodiments of the present application, not all of the embodiments. Based on the embodiments in the present application, all other embodiments obtained by those skilled in the art without creative efforts shall fall within the protection scope of the present application.

Figure 1:
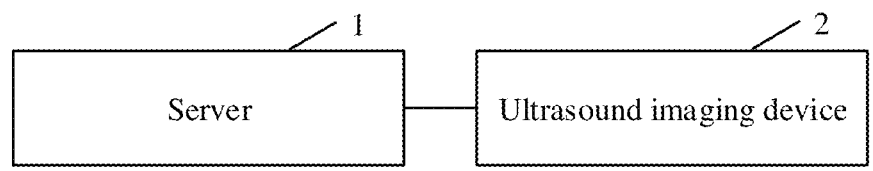
FIG. 1 is a schematic diagram of a scene applicable for embodiments of the present application.

FIG. 1 is a schematic diagram of a scene applicable for an embodiment of the present application. As shown in FIG. 1, a scene applicable for an embodiment of the present application includes a server 1 and an ultrasound imaging device 2. There is a communication connection relationship between the server 1 and the ultrasound imaging device 2.

Specifically, the ultrasound imaging device 2 is configured to acquire a first three-dimensional local image sequence including microbubbles. The server 1 is configured to perform at least one thinning operation on the first three-dimensional local image sequence, the thinning operation being configured to enhance motion trajectories of microbubbles; and perform an image reconstruction operation based on the first three-dimensional local image sequence subjected to the at least one thinning operation, so as to generate a three-dimensional super-resolution image. That is, the scene realizes a super-resolution reconstruction method for three-dimensional contrast-enhanced ultrasound images.

Since the above scene shown in FIG. 1 realizes the super-resolution reconstruction method for three-dimensional contrast-enhanced ultrasound images using the server 1, not only adaptability of the scene is improved, but also calculation amount of the ultrasound imaging device 2 is effectively reduced.

Figure 2:
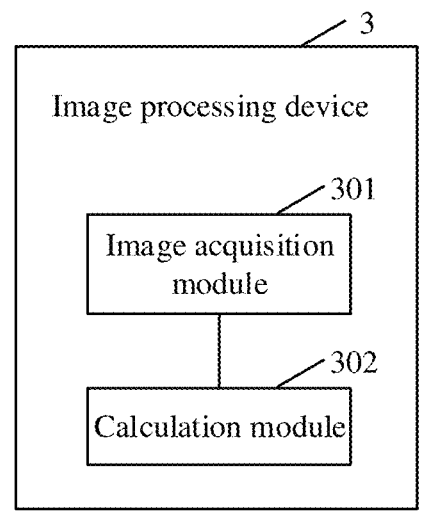
FIG. 2 is a schematic diagram of another scene applicable for embodiments of the present application.

Exemplarily, embodiments of the present application are also applicable to another scene. FIG. 2 is a schematic diagram of another scene applicable for an embodiment of the present application. Specifically, the scene includes an image processing device 3, the image processing device 3 including an image acquisition module 301 and a calculation module 302. There is a communication connection between the image acquisition module 301 and the calculation module 302.

Specifically, the image acquisition module 301 in the image processing device 3 may be configured to perform functions of the ultrasound imaging device 2 in the scene shown in FIG. 1. The calculation module 302 in the image processing device 3 may be configured to perform functions of the server 1 in the scene shown in FIG. 1. Embodiments of the present application will not be repeated here.

Since the above scene shown in FIG. 2 realizes the super-resolution reconstruction method for three-dimensional contrast-enhanced ultrasound images using the image processing device 3 with no need to perform data transmission operations using related devices such as servers, the above scene shown in FIG. 2 is capable of ensuring the reconstruction efficiency of super-resolution imaging for three-dimensional contrast-enhanced ultrasound images.

Figure 3:
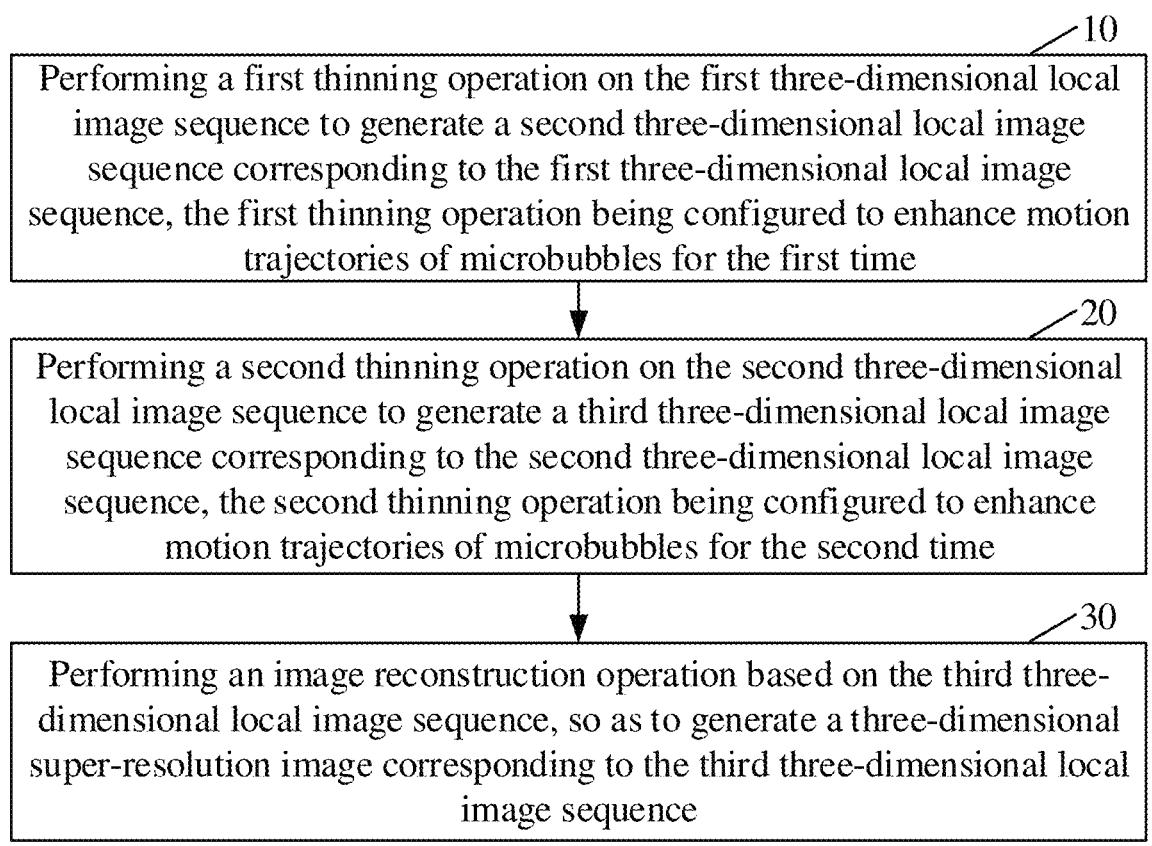
FIG. 3 is a schematic flowchart of a super-resolution reconstruction method for three-dimensional contrast-enhanced ultrasound images according to an exemplary embodiment of the present application.

FIG. 3 is a schematic flowchart of a super-resolution reconstruction method for three-dimensional contrast-enhanced ultrasound images according to an exemplary embodiment of the present application. As shown in FIG. 3, the super-resolution reconstruction method for three-dimensional contrast-enhanced ultrasound images according to embodiments of the present application include the following steps.

Step 10: performing a first thinning operation on the first three-dimensional local image sequence to generate a second three-dimensional local image sequence corresponding to the first three-dimensional local image sequence, the first thinning operation being used to enhance motion trajectories of microbubbles for a first time.

Exemplarily, the first three-dimensional local image sequence mentioned in Step 10 is a three-dimensional local image sequence including microbubbles acquired by an ultrasound imaging device. That is, the first three-dimensional local image sequence includes a plurality of first three-dimensional local images, and the first three-dimensional local image includes microbubble areas.

By performing the first thinning operation and a second thinning operation on the first three-dimensional local image sequence, a three-dimensional super-resolution image including an overall structure of blood vessels (such as blood vessel structure in tumor) may be reconstructed. That is, in the embodiment of the present application, the meaning of "local" is that each first three-dimensional local image represents a local image content of the three-dimensional super-resolution image. After corresponding processing of all the first three-dimensional local images, the three-dimensional super-resolution image including the overall structure may be generated.

Exemplarily, the first thinning operation is configured to enhance motion trajectories of microbubbles, for example, enhancing central (central axis) regions of the microbubbles. In addition, the first thinning operation mentioned in the embodiments of the present application may suppress noise in a background area. A plurality of frames of second three-dimensional local images included in the second three-dimensional local image sequence are obtained by performing the first thinning operation on a plurality of frames of the first three-dimensional local images in the first three-dimensional local image sequence frame by frame. For example, the first three-dimensional local image sequence is characterized as $S_R=\{S_R^j|j=1,2,\ldots N\}$, and the second three-dimensional local image sequence is characterized as $S_G=\{S_G^j|j=1,2,\ldots N\}$.

Step 20: performing a second thinning operation on the second three-dimensional local image sequence to generate a third three-dimensional local image sequence corresponding to the second three-dimensional local image sequence, the second thinning operation being configured to enhance motion trajectories of the microbubbles for a second time.

Exemplarily, the second thinning operation is configured to enhance the motion trajectories of the microbubbles based on a non-localization-based manner. For example, instead of locating the microbubble areas in images, the motion trajectories of the microbubbles are enhanced by performing a degree of radial symmetry estimation operation on pixels in the second three-dimensional local images of the second three-dimensional local image sequence.

Exemplarily, the embodiments of the present application do not limit the specific implementation of the second thinning operation mentioned in Step 20, as long as the second thinning operation can enhance the motion trajectories of the microbubbles.

Step 30: performing an image reconstruction operation based on a third three-dimensional local image sequence, so as to generate a three-dimensional super-resolution image corresponding to the third three-dimensional local image sequence.

In an embodiment of the present application, the performing an image reconstruction operation based on a third three-dimensional local image sequence, so as to generate a three-dimensional super-resolution image corresponding to the third three-dimensional local image sequence, includes: performing an accumulation operation on the third three-dimensional local images in the third three-dimensional local image sequence based on image sequence information corresponding to the third three-dimensional local image sequence, so as to generate the three-dimensional super-resolution image.

In an actual application, firstly, the first thinning operation is performed on the first three-dimensional local image sequence to generate the second three-dimensional local image sequence corresponding to the first three-dimensional local image sequence. Then, the second thinning operation is performed on the second three-dimensional local image sequence to generate the third three-dimensional local image sequence corresponding to the second three-dimensional local image sequence. Then, the image reconstruction operation is performed based on the third three-dimensional local image sequence, so as to generate the three-dimensional super-resolution image corresponding to the third three-dimensional local image sequence.

The super-resolution reconstruction method for the three-dimensional contrast-enhanced ultrasound images according to embodiments of the present application, by means of respectively performing the first thinning operation and the second thinning operation on the first three-dimensional local image sequence, motion trajectories of microbubbles are highlighted, thereby improving a signal-to-noise ratio of an image. Compared with a prior super-resolution reconstruction method for the three-dimensional contrast-enhanced ultrasound images, embodiments of the present application may greatly improve efficiency and precision of the three-dimensional super-resolution image reconstruction operation.

Exemplarily, the first thinning operation and the second thinning operation mentioned in the embodiment shown in FIG. 3 are not limited to coexist. For example, there may be only the first thinning operation or only the second thinning operation as long as the motion trajectories of microbubbles can be highlighted, thereby improving the localization precision of the microbubbles in the three-dimensional images.

For example, the super-resolution reconstruction method for three-dimensional contrast-enhanced ultrasound images includes: performing at least one thinning operation on the first three-dimensional local image sequence, the thinning operation being configured to enhance motion trajectories of microbubbles; and performing the image reconstruction operation based on the first three-dimensional local image sequence subjected to the at least one thinning operation, so as to generate the three-dimensional super-resolution image.

Figure 4:
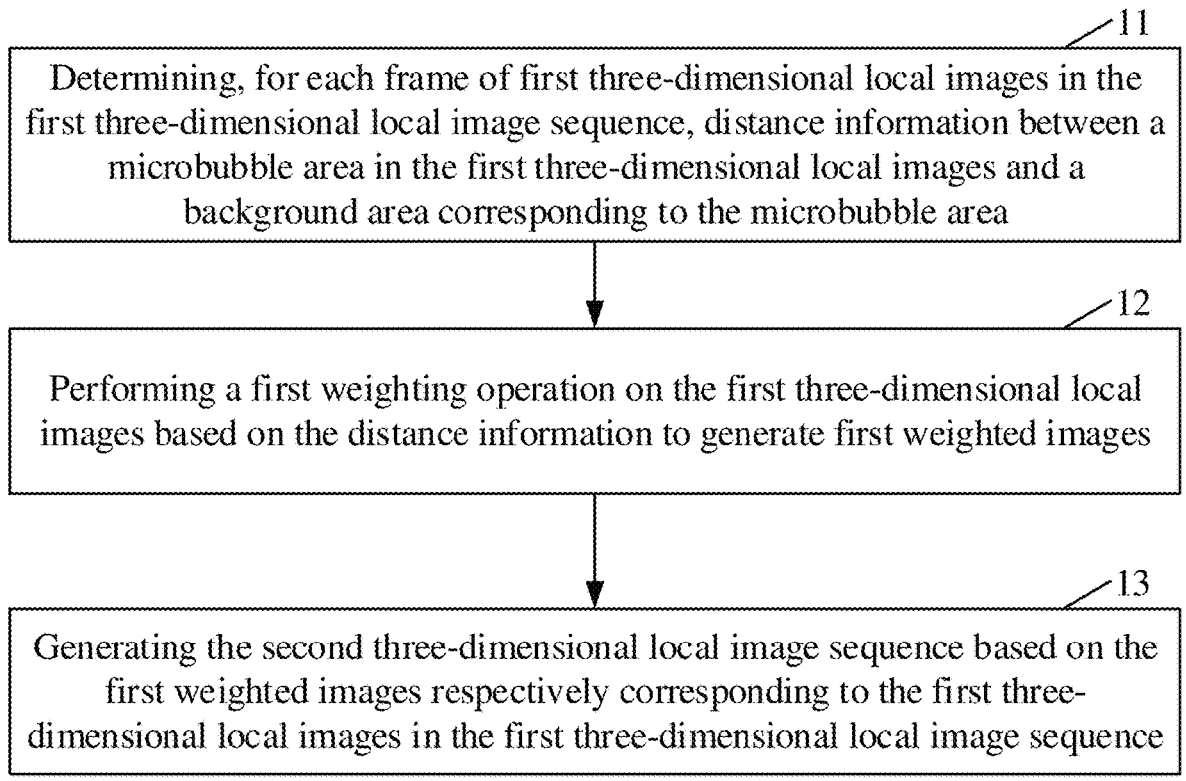
FIG. 4 is a schematic flowchart for performing a first thinning operation on a first three-dimensional local image sequence to generate a second three-dimensional local image sequence corresponding to the first three-dimensional local image sequence according to an exemplary embodiment of the present application.

FIG. 4 is a schematic flowchart for performing a first thinning operation on a first three-dimensional local image sequence to generate a second three-dimensional local image sequence corresponding to the first three-dimensional local image sequence according to an exemplary embodiment of the present application. The embodiment of the present application is extended based on the embodiment of the present application shown in FIG. 3. Differences between the embodiment of the present application and the embodiment shown in FIG. 3 are emphatically described below, and similarities may not be described repeatedly.

As shown in FIG. 4, in the super-resolution reconstruction method for three-dimensional contrast-enhanced ultrasound images according to an embodiment of the present application, the step performing a first thinning operation on the first three-dimensional local image sequence to generate a second three-dimensional local image sequence corresponding to the first three-dimensional local image sequence includes the following steps.

Step 11: determining, for each frame of first three-dimensional local images in the first three-dimensional local image sequence, distance information between a microbubble area in the first three-dimensional local image and a background area corresponding to the microbubble area.

Exemplarily, the microbubble area refers to an image area corresponding to microbubbles in the first three-dimensional local image, and the background area refers to a background image area that does not include microbubbles in the first three-dimensional local image.

Exemplarily, since the above-mentioned first three-dimensional local images are three-dimensional images, the distance information is distance information of a three-dimensional space. And the microbubble area corresponds to a plurality of pixel coordinates arranged in a three-dimensional space.

Figure 5:
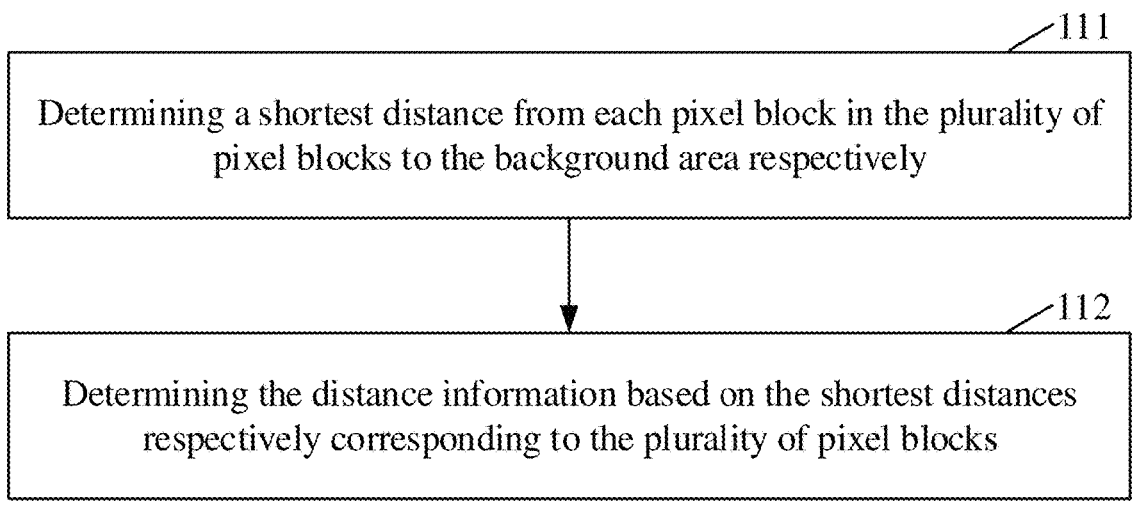
FIG. 5 is a schematic flowchart for determining distance information between a microbubble area in the first three-dimensional local image and a background area corresponding to the microbubble area according to an exemplary embodiment of the present application.

FIG. 5 is a schematic flowchart for determining distance information between a microbubble area in the first three-dimensional local image and a background area corresponding to the microbubble area according to an exemplary embodiment of the present application. As shown in FIG. 5, in the embodiment of the present application, the microbubble area includes a plurality of pixel blocks. The determining distance information between a microbubble area in the first three-dimensional local image and a background area corresponding to the microbubble area (Step 11) includes the following steps.

Step 111: determining a shortest distance from each pixel block in the plurality of pixel blocks to the background area respectively.

Step 112; determining the distance information based on the shortest distances respectively corresponding to the plurality of pixel blocks.

Exemplarily, the shortest distance mentioned in Step 111 is Euclidean distance or Manhattan distance, preferably Euclidean distance.

For example, the pixel blocks mentioned above are individual pixel units. Correspondingly, pixel coordinates corresponding to the pixel blocks are pixel coordinates corresponding to the pixel units. For another example, the pixel blocks mentioned above are pixel blocks formed by a plurality of adjacent pixel units. Correspondingly, pixel coordinates corresponding to the pixel blocks are pixel coordinates at center points of the plurality of pixel units.

Step 12; performing a first weighting operation on the first three-dimensional local images based on the distance information to generate first weighted images.

In an embodiment of the present application, based on the pixel coordinates corresponding to the microbubble area, a pixel grayscale value and a shortest distance corresponding to each pixel coordinate are respectively determined. Then, the shortest distance is multiplied by the pixel grayscale value to determine a new pixel grayscale value corresponding to the pixel coordinate, and then the first weighted image corresponding to the first three-dimensional local image is finally determined.

The shortest distance between a central region of the microbubble and a reference region is larger than that of the marginal region of the microbubble. Therefore, after performing the first weighting operation on the first three-dimensional local images based on the distance information, the central region (i.e. a central axis region along microbubble trajectory) of the microbubbles of the first three-dimensional local image may be effectively highlighted (i.e. enhanced), and the noise in the background area is removed, so as to achieve a purpose of enhancing the motion trajectories of the microbubbles.

Step 13: generating the second three-dimensional local image sequence based on the first weighted images respectively corresponding to the first three-dimensional local images in the first three-dimensional local image sequence.

The super-resolution reconstruction method for three-dimensional contrast-enhanced ultrasound images according to embodiments of the present application, effectively highlights (i.e. enhances) the central region of the microbubbles in the first three-dimensional local image sequence, removes the noise in the background area, and improves a signal-to-noise ratio of the image, and then highlights (i.e. enhances) three-dimensional motion trajectories of microbubbles along the vessel in the moving directions of microbubbles, thereby improving efficiency and precision of three-dimensional super-resolution reconstruction.

In an embodiment of the present application, before the performing a first weighting operation on the first three-dimensional local images based on the distance information to generate first weighted images, the method further includes: performing binarization processing on the first three-dimensional local images based on the microbubble area and the background area to generate binarized images. The performing a first weighting operation on the first three-dimensional local images based on the distance information to generate first weighted images includes: performing the first weighting operation on the binarized images based on the distance information corresponding to the first three-dimensional local images to generate the first weighted images.

Binarizing the first three-dimensional local images based on the embodiment of the present application may simplify the calculation procedure of the step of generating the first weighted images corresponding to the first three-dimensional local images, speed up the calculation process, and further improve the reconstruction efficiency.

An application effect of the first thinning operation mentioned in the embodiment shown in FIG. 4 and FIG. 5 will be described below with reference to FIG. 6, FIG. 7a and FIG. 7b. It should be noted that, in order to clearly present the application effect of the first thinning operation, FIG. 6, FIG. 7a and FIG. 7b take a two-dimensional image including a rectangle (analogously as a microbubble) as an example to show. The two-dimensional image is used here for convenience and clarity only.

Figure 6:
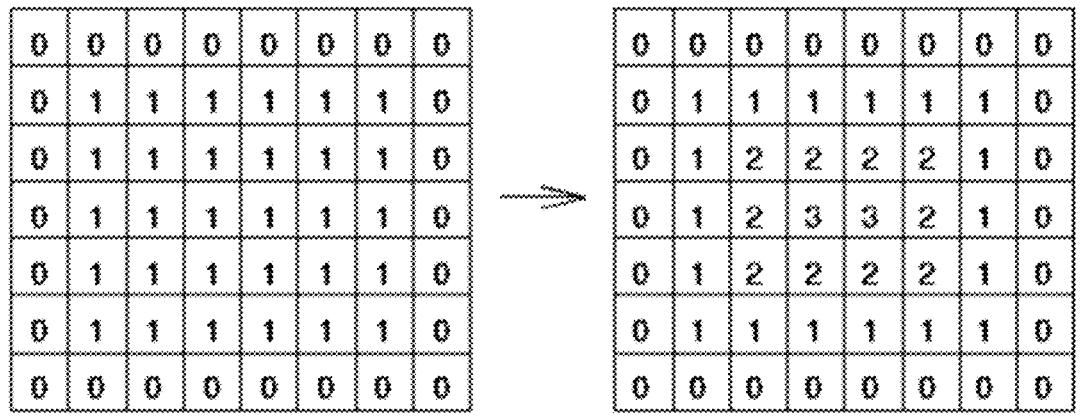
FIG. 6 is a schematic diagram of a process of generating a first weighted image according to an exemplary embodiment of the present application.

FIG. 6 is a schematic diagram of a process of generating first weighted images according to an exemplary embodiment of the present application. Specifically, an image on the left side of FIG. 6 is a pixel distribution diagram of a two-dimensional image. The pixel values of pixel coordinates corresponding to the rectangular area (analogously the microbubble area) is set to 1, and the pixel values of the pixel coordinates corresponding to the background area is set to 0. An image on the right side of FIG. 6 is a pixel distribution diagram of the first weighted image obtained by performing distance weighting (i.e., the first weighting operation) on the image on the left side of FIG. 6. In the embodiment of the present application, the shortest distance is determined by using the "chessboard distance". For each pixel coordinate corresponding to the rectangle, a weighted value (i.e., a new pixel value) corresponding to the pixel coordinate is obtained by multiplying the shortest distance corresponding to the pixel coordinate by the pixel value corresponding to the pixel coordinate, and finally the image on the right side of FIG. 6 is obtained.

Figure 7A:
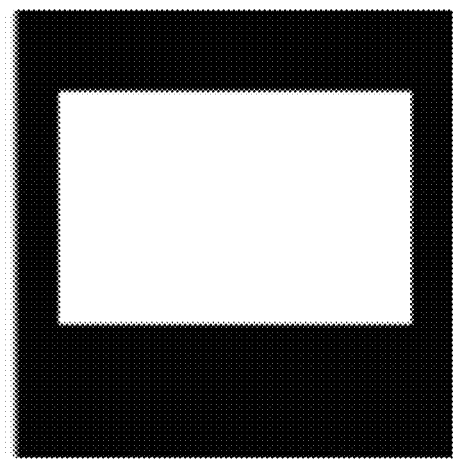
FIG. 7a and FIG. 7b are schematic diagrams of weighting effect of a first weighting operation according to an exemplary embodiment of the present application.
Figure 7B:
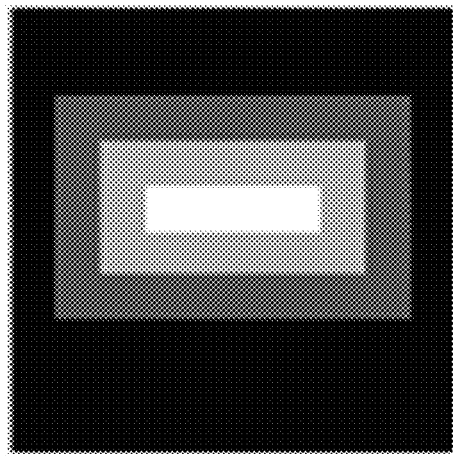

FIG. 7a and FIG. 7b are schematic diagrams of weighting effect of a first weighting operation according to an exemplary embodiment of the present application. Specifically, FIG. 7a shows imaging effect corresponding to the image on the left side of FIG. 6. FIG. 7b shows imaging effect corresponding to the image on the right side of FIG. 6. As shown in FIG. 7a and FIG. 7b, it can be clearly seen that after a first decoupling operation, the central region of the rectangle in the two-dimensional image is enhanced (i.e., highlighted), and the marginal region is weakened. It can be seen that, after a first thinning operation, the central regions of the microbubbles in the first three-dimensional local image may be enhanced (i.e., may be highlighted), and the marginal regions may be weakened. Based on the effects obtained in the above embodiment, it can be inferred that after the first thinning operation, a large amount of noise (such as background noise) in the image is removed, and the motion trajectories of the microbubbles is enhanced.

Figure 8:
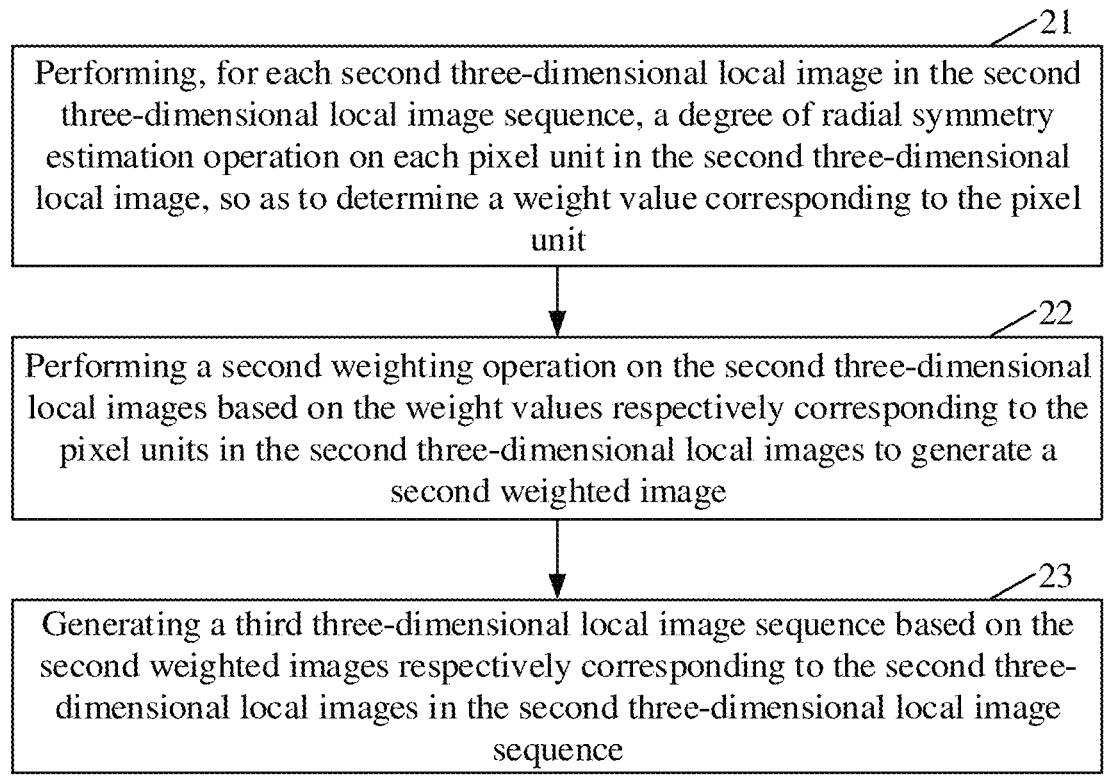
FIG. 8 is a schematic flowchart for performing a second thinning operation on the second three-dimensional local image sequence to generate a third three-dimensional local image sequence corresponding to the second three-dimensional local image sequence according to an exemplary embodiment of the present application.

FIG. 8 is a schematic flowchart for performing a second thinning operation on a second three-dimensional local image sequence to generate a third three-dimensional local image sequence corresponding to the second three-dimensional local image sequence according to an exemplary embodiment of the present application. The embodiment of the present application is extended based on the embodiment of the present application shown in FIG. 3. Differences between the embodiment of the present application and the embodiment shown in FIG. 3 are emphatically described below, and similarities may not be described repeatedly.

As shown in FIG. 8, in the super-resolution reconstruction method for three-dimensional contrast-enhanced ultrasound images according to an embodiment of the present application, the performing a second thinning operation on the second three-dimensional local image sequence to generate a third three-dimensional local image sequence corresponding to the second three-dimensional local image sequence includes the following steps.

Step 21: performing, for each second three-dimensional local image in the second three-dimensional local image sequence, a degree of radial symmetry estimation operation on each pixel unit in the second three-dimensional local images, so as to determine a weight value corresponding to the pixel unit.

Exemplarily, the degree of radial symmetry estimation operation mentioned in Step 21 is implemented based on a degree of radial symmetry calculation method in super-resolution radial fluctuations (Zhang, J. J Ultrasound Med. 2020).

Exemplarily, a number of sampling points is 12 and a sampling radius is 1 in the degree of radial symmetry operation. An inventor of the present application found that after setting the number of sampling points to 12 and the sampling radius to 1 in the degree of radial symmetry estimation operation, precision of determined three-dimensional motion trajectories of the microbubbles are significantly improved.

Exemplarily, the pixel unit mentioned in Step 21 is a pixel point in the second three-dimensional local image.

Step 22: performing second weighting operation on the second three-dimensional local images based on the weight values respectively corresponding to the pixel units in the second three-dimensional local images to generate second weighted images.

Step 23: generating a third three-dimensional local image sequence based on the second weighted images respectively corresponding to the second three-dimensional local images in the second three-dimensional local image sequence.

The super-resolution reconstruction method for three-dimensional contrast-enhanced ultrasound images according to an embodiment of the present application, for each second three-dimensional local image in the second three-dimensional local image sequence, by performing the degree of radial symmetry estimation operation on each pixel unit in the second three-dimensional local images, determine the weight values corresponding to the pixel units. The second weighted images are generated by performing the second weighting operation on the second three-dimensional local images based on the weight values respectively corresponding to the pixel units in the second three-dimensional local images. And the second thinning operation is performed on the second three-dimensional local image sequence through the method of generating the third three-dimensional local image sequence based on the second weighted images respectively corresponding to the second three-dimensional local images in the second three-dimensional local image sequence, to generate the third three-dimensional local image sequence corresponding to the second three-dimensional local image sequence.

Since after performing the degree of radial symmetry estimation operation on each pixel unit in the second three-dimensional local images, the motion trajectories of the microbubbles in the second three-dimensional local images may be further enhanced, the embodiments of the present application further improve the efficiency and precision of the super-resolution reconstruction.

The following describes beneficial effect obtaining principle and specific calculation examples corresponding to the embodiment shown in FIG. 8 with reference to FIG. 9a to FIG. 9c, FIG. 10a, FIG. 10b, and FIG. 11.

Figures 9A, 9B, 9C:
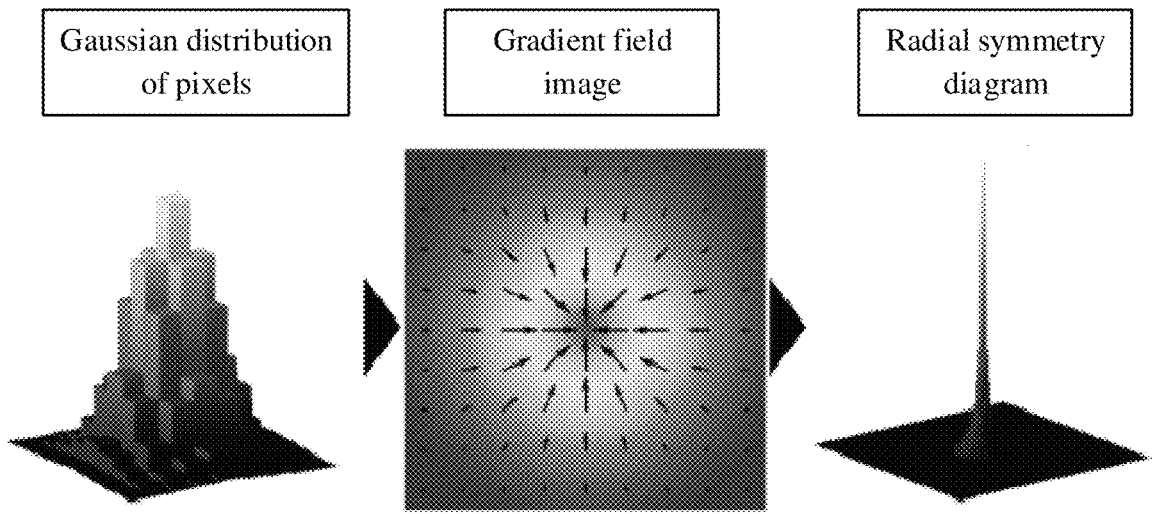
FIG. 9a to FIG. 9c are schematic diagrams for intuitive explanation of a degree of radial symmetry estimation operation.

FIG. 9a to FIG. 9c are schematic diagrams for intuitive explanation of a degree of radial symmetry estimation operation. Specifically, FIG. 9a is a schematic diagram of a Gaussian distribution of pixels corresponding to a second three-dimensional local image in a second three-dimensional local image sequence including microbubbles. In ultrasound imaging technology, the point spread function of a microbubble may be viewed as a Gaussian distribution. The height of each pixel column represents a pixel value, and a higher position corresponds to a larger pixel value. The microbubbles in the image show grayscale features that the middle part is brighter and the closer to the edge, the darker of the grayscale value.

If a gradient field is calculated for the second three-dimensional local image corresponding to FIG. 9a, a gradient field image shown in FIG. 9b may be obtained. Based on the gradient field image shown in FIG. 9b, it can be found that if all the gradient vectors (black arrows shown in FIG. 9b) are extended, they will intersect at a center point of the microbubble, that is, the gradient at the center is convergent. This also means that if a straight line is drawn arbitrarily through the center point, the gradient vectors on left and right of the straight line are completely symmetrical, and the further away from the center point, the weaker the symmetry. Therefore, if the degree of radial symmetry of each pixel point in FIG. 9a is estimated, a degree of radial symmetry diagram shown in FIG. 9c will be obtained.

Therefore, after weighting the degree of radial symmetry diagram shown in FIG. 9c to the second three-dimensional local image, the third three-dimensional local image in which the central region of the microbubble area is enhanced and the marginal region of the microbubble area is weakened (suppressed) is obtained. The third three-dimensional local images correspond to the second three-dimensional local images.

Figure 10A:
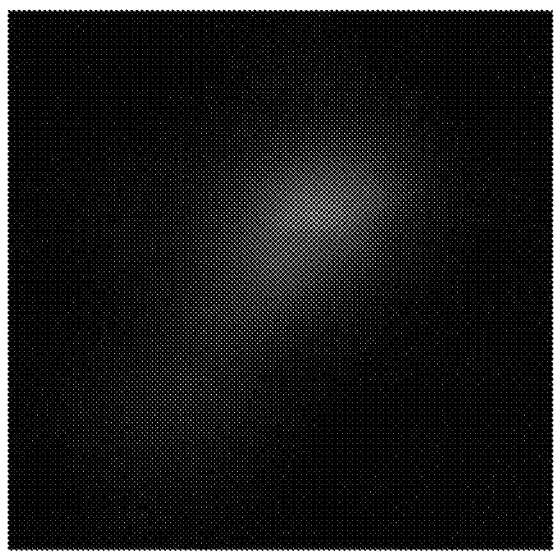
FIG. 10a and FIG. 10b are schematic diagrams of weighting effect after a degree of radial symmetry estimation operation is performed on microbubbles.
Figure 10B:
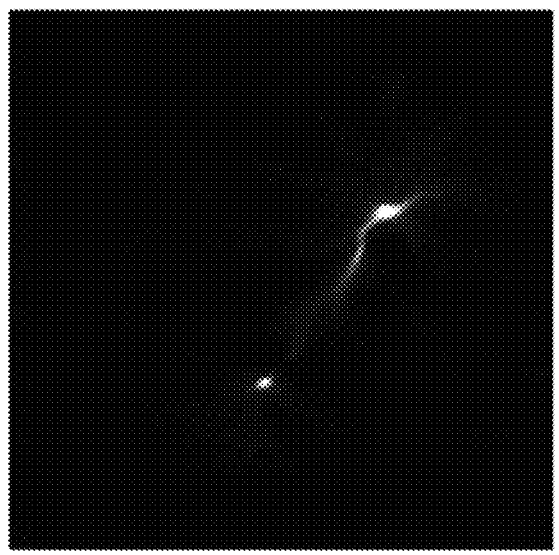

FIG. 10a and FIG. 10b are schematic diagrams of weighting effect after a degree of radial symmetry estimation operation is performed on the microbubbles. In an actual scene, because the microbubbles are moving, the microbubbles are elongated along a flowing direction as shown in FIG. 10a. Then, after the degree of radial symmetry estimation operation is performed on the image shown in FIG. 10a by using the second thinning operation mentioned in the above embodiment, a second weighted image shown in FIG. 10b may be obtained. In FIG. 10b, the motion trajectories of the microbubbles are clearly preserved.

A calculation process of the degree of radial symmetry estimation operation will be described below with reference to specific examples.

For an image plane I(x,y), the gradient may be calculated based on the following equations (1) and (2).

$$G_x(x, y) = \frac{\partial I(x, y)}{\partial x} \tag{1}$$

$$G_y(x, y) = \frac{\partial I(x, y)}{\partial y} \tag{2}$$

The following takes $(x_c, y_c)$ as an example to illustrate how to calculate an estimated degree of radial symmetry at $(x_c, y_c)$.

Firstly, taking N points uniformly distributed on a ring with $(x_c, y_c)$ as a center of a circle and radius r as sample points. Among them, N is an arbitrarily defined variable used to determine a number of gradient samples. Exemplarily, N is set to 12, and $(x'_i, y'_i)$ is one of the sample points.

Secondly, determining a gradient line at $(x'_i, y'_i)$. Specifically, gradient vectors $G_{xi}$ and $G_{yi}$ at $(x'_i, y'_i)$ are obtained from original image gradient vectors $G_x$ and $G_y$. The gradient line at $(x'_i, y'_i)$ is determined by a gradient line formula at sample point $(x'_i, y'_i)$ given in the following formula (3).

$$0 = (x - x'_i)G_{yi} - (y - y'_i)'G_{xi} \quad (3)$$

Then, calculating the minimum vertical distance from point $(x_c, y_c)$ to the gradient line passing through $(x'_i, y'_i)$ based on the following formula (4).

$$d_i = \frac{|(x_c - x'_i)G_{yi} - (y_c - y'_i)G_{xi}|}{\sqrt{G_{xi}^2 + G_{yj}^2}} \quad (4)$$

Calculating an included angle between vector $G_i = (G_{xi}\hat{x}, G_{yi}\hat{y})$ and vector $r_i = (r_{xi}\hat{x} r_{yi}\hat{y})$ based on the following formula (5).

$$\theta = \frac{G_i \cdot r_i}{|G_i| |r_i|} \quad (5)$$

Finally, determining the convergence degree of point $(x_c, y_c)$ at point $(x'_i, y'_i)$ based on the following formula (6).

$$c_i = \text{sgn}(\theta)\left[\frac{(1-d_i)}{|r_i|}\right]^2 \quad (6)$$

If $(x_c, y_c)$ is a center point of Gaussian distribution, gradient extension lines of all sample points pass through the center point, so $d_i$ will be 0, and $c_i$ will be a maximum value.

If the convergence degrees of the N sample points are calculated and averaged respectively, the estimated degree of radial symmetry may be obtained based on the following formula (7).

$$R_t(x, y) = \frac{1}{N}\sum_{i=1}^{N} c_i \quad (7)$$

Figure 11:
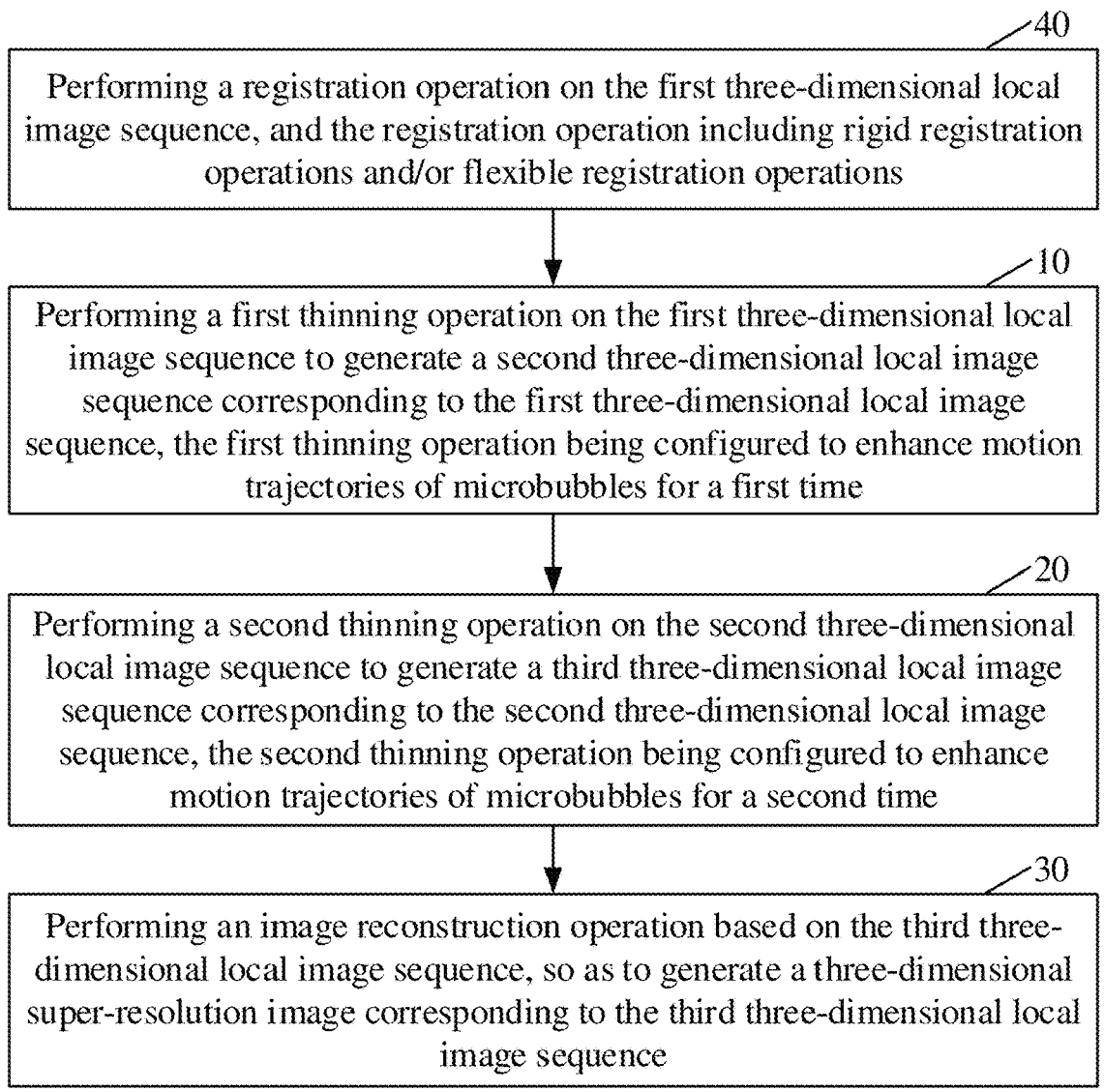
FIG. 11 is a schematic flowchart of a super-resolution reconstruction method for three-dimensional contrast-enhanced ultrasound images according to another exemplary embodiment of the present application.

FIG. 11 is a schematic flowchart of a super-resolution reconstruction method for a three-dimensional contrast-enhanced ultrasound images according to another exemplary embodiment of the present application. The embodiment of the present application is extended based on the embodiment of the present application shown in FIG. 3. Differences between the embodiment of the present application and the embodiment shown in FIG. 3 are emphatically described below, and similarities may not be described repeatedly.

As shown in FIG. 11, in the super-resolution reconstruction method for the three-dimensional contrast-enhanced ultrasound images according to an embodiment of the present application, before the performing a first thinning operation on a first three-dimensional local image sequence to generate a second three-dimensional local image sequence corresponding to the first three-dimensional local image sequence, the following steps are further included.

Step 40: performing a registration operation on the first three-dimensional local image sequence, the registration operation including rigid registration operations and/or flexible registration operations.

Exemplarily, a three-dimensional Morphon multi-scale registration method is used to perform the registration operation on the first three-dimensional local image sequence. Exemplarily, a decomposition scale is 3 layers. A deformation field is processed by Gaussian kernel smoothing, and a size of Gaussian kernel is 10 pixels.

In an actual application process, firstly, the registration operation on the first three-dimensional local image sequence is performed. Then, the first thinning operation on the first three-dimensional local image sequence is performed to generate the second three-dimensional local image sequence corresponding to the first three-dimensional local image sequence. Then, the second thinning operation on the second three-dimensional local image sequence is performed to generate the third three-dimensional local image sequence corresponding to the second three-dimensional local image sequence. Finally, the image reconstruction operation is performed based on the third three-dimensional local image sequence, so as to generate the three-dimensional super-resolution image corresponding to the third three-dimensional local image sequence.

The super-resolution reconstruction method for three-dimensional contrast-enhanced ultrasound images according to embodiments of the present application, by performing the registration operation on the first three-dimensional local image sequence before performing the first thinning operation and the second thinning operation on the three-dimensional local image sequence, effectively suppresses the influence of tissue motion (such as motion caused by breath) on the accuracy of microbubble localization, thereby further improving the accuracy of microbubble localization, and further improving the precision of super-resolution reconstruction.

Figure 12:
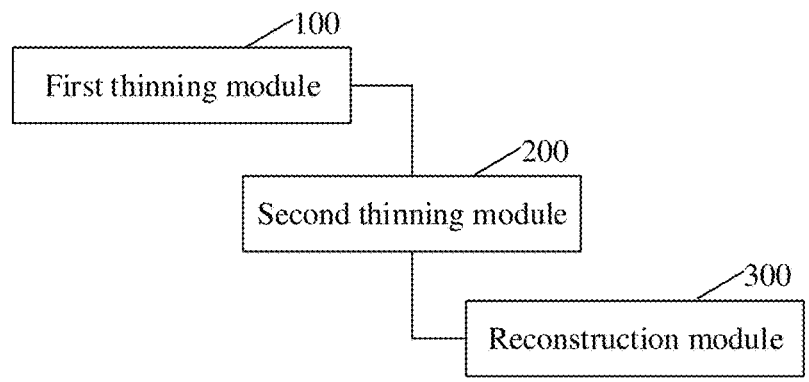
FIG. 12 is a schematic structural diagram of a super-resolution reconstruction apparatus for three-dimensional contrast-enhanced ultrasound images according to an exemplary embodiment of the present application.

FIG. 12 is a schematic structural diagram of a super-resolution reconstruction apparatus for three-dimensional contrast-enhanced ultrasound images according to an exemplary embodiment of the present application. As shown in FIG. 12, the super-resolution reconstruction apparatus for the three-dimensional contrast-enhanced ultrasound images provided by an embodiment of the present application includes the following modules.

A first thinning module 100 is configured to perform a first thinning operation on a first three-dimensional local image sequence to generate a second three-dimensional local image sequence corresponding to the first three-dimensional local image sequence. The first thinning operation is configured to enhance motion trajectories of microbubbles for a first time.

A second thinning module 200 is configured to perform a second thinning operation on the second three-dimensional local image sequence to generate a third three-dimensional local image sequence corresponding to the second three-dimensional local image sequence. The second thinning operation is configured to enhance motion trajectories of microbubbles for a second time.

A reconstruction module 300 is configured to perform an image reconstruction operation based on the third three-dimensional local image sequence, so as to generate a three-dimensional super-resolution image corresponding to the third three-dimensional local image sequence.

Similarly, a super-resolution reconstruction apparatus for three-dimensional contrast-enhanced ultrasound images provided by another embodiment of the present application includes: a thinning module and a reconstruction module signally connected to the thinning module. The thinning module is configured to perform at least one thinning operation on the first three-dimensional local image sequence. The thinning operation is configured to enhance motion trajectories of microbubbles. The reconstruction module is configured to perform an image reconstruction operation based on the first three-dimensional local image sequence subjected to the at least one thinning operation, so as to generate the three-dimensional super-resolution image.

Figure 13:
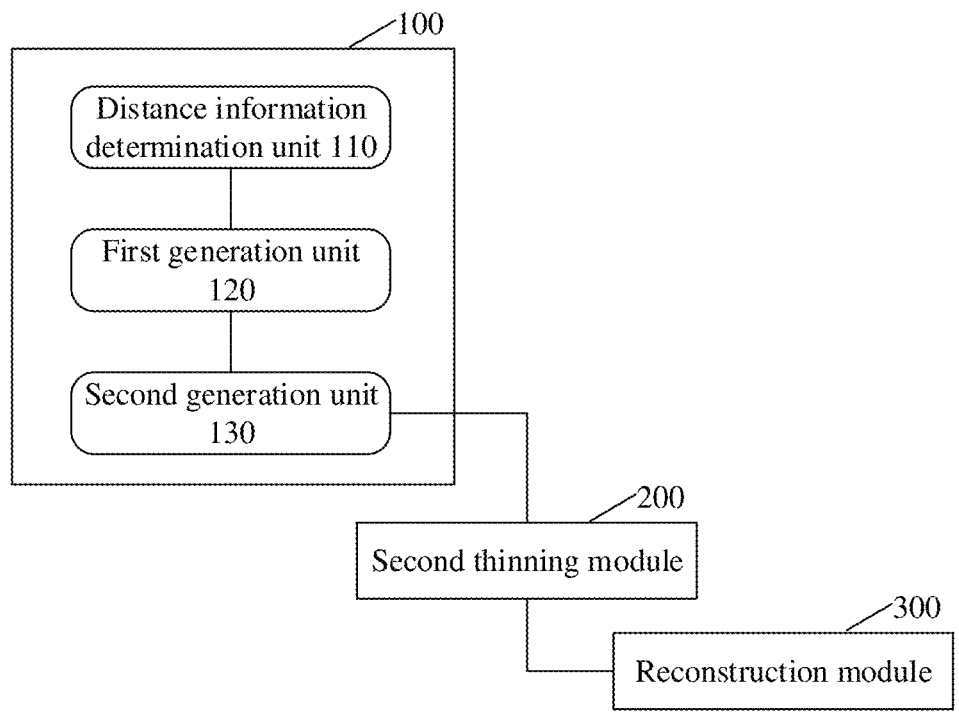
FIG. 13 is a schematic structural diagram of a super-resolution reconstruction apparatus for three-dimensional contrast-enhanced ultrasound images according to another exemplary embodiment of the present application.

FIG. 13 is a schematic structural diagram of a super-resolution reconstruction apparatus for three-dimensional contrast-enhanced ultrasound images according to another exemplary embodiment of the present application. The embodiment of the present application is extended based on the embodiment of the present application shown in FIG. 12. Differences between the embodiment of the present application and the embodiment shown in FIG. 12 are emphatically described below, and similarities may not be described repeatedly.

As shown in FIG. 13, in the super-resolution reconstruction apparatus for three-dimensional contrast-enhanced ultrasound images according to an embodiment of the present application, a first thinning module 100 includes the following units.

A distance information determination unit 110 is configured to determine, for each frame of first three-dimensional local images in the first three-dimensional local image sequence, distance information between a microbubble area in the first three-dimensional local image and a background area corresponding to the microbubble area.

A first generation unit 120 is configured to perform a first weighting operation on the first three-dimensional local images based on the distance information to generate first weighted images A second generation unit 130 is configured to generate a second three-dimensional local image sequence based on the first weighted images respectively corresponding to the first three-dimensional local images in the first three-dimensional local image sequence.

In an embodiment of the present application, the distance information determination unit 110 is further configured to: determine a shortest distance from each pixel block in the plurality of pixel blocks to the background area respectively, and determine the distance information based on the shortest distances respectively corresponding to the plurality of pixel blocks.

Figure 14:
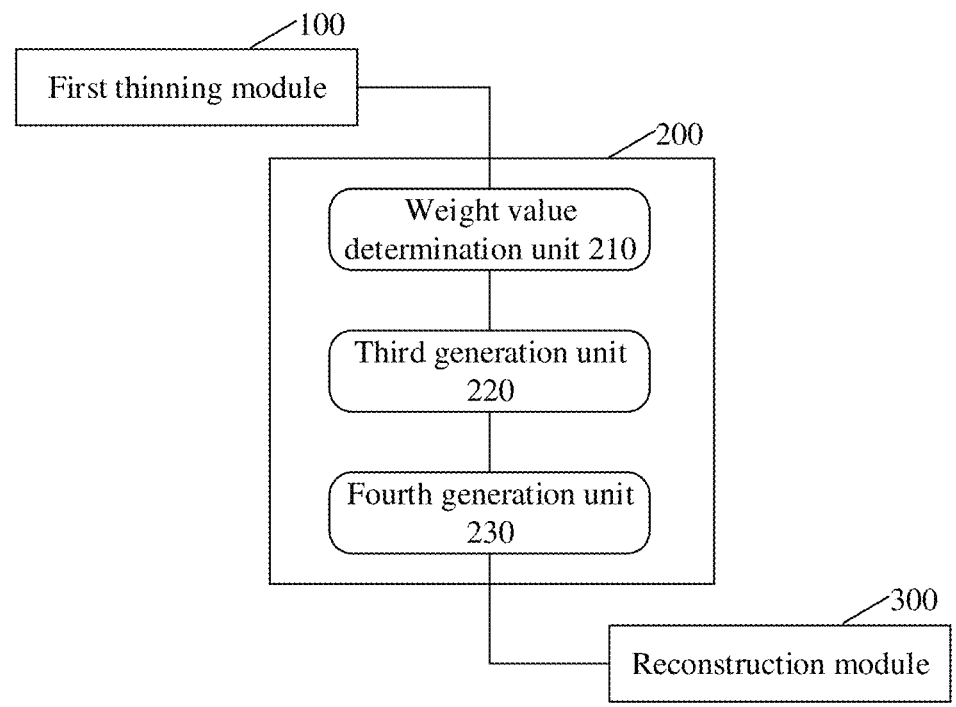
FIG. 14 is a schematic structural diagram of a super-resolution reconstruction apparatus for three-dimensional contrast-enhanced ultrasound images according to another exemplary embodiment of the present application.

FIG. 14 is a schematic structural diagram of a super-resolution reconstruction apparatus for three-dimensional contrast-enhanced ultrasound images according to another exemplary embodiment of the present application. The embodiment of the present application is extended based on the embodiment of the present application shown in FIG. 12. Differences between the embodiment of the present application and the embodiment shown in FIG. 12 are emphatically described below, and similarities may not be described repeatedly.

As shown in FIG. 14, in the super-resolution reconstruction apparatus for three-dimensional contrast-enhanced ultrasound images according to an embodiment of the present application, a second thinning module 200 includes the following units.

A weight value determination unit 210 is configured to perform, for each frame of second three-dimensional local images in the second three-dimensional local image sequence, a degree of radial symmetry estimation operation on each pixel unit in the second three-dimensional local images, so as to determine a weight value corresponding to the pixel unit.

A third generation unit 220 is configured to perform a second weighting operation on the second three-dimensional local images based on the weight values respectively corresponding to the pixel units in the second three-dimensional local images to generate second weighted images.

A fourth generation unit 230 is configured to generate a third three-dimensional local image sequence based on the second weighted images respectively corresponding to the second three-dimensional local images in the second three-dimensional local image sequence.

Figure 15:
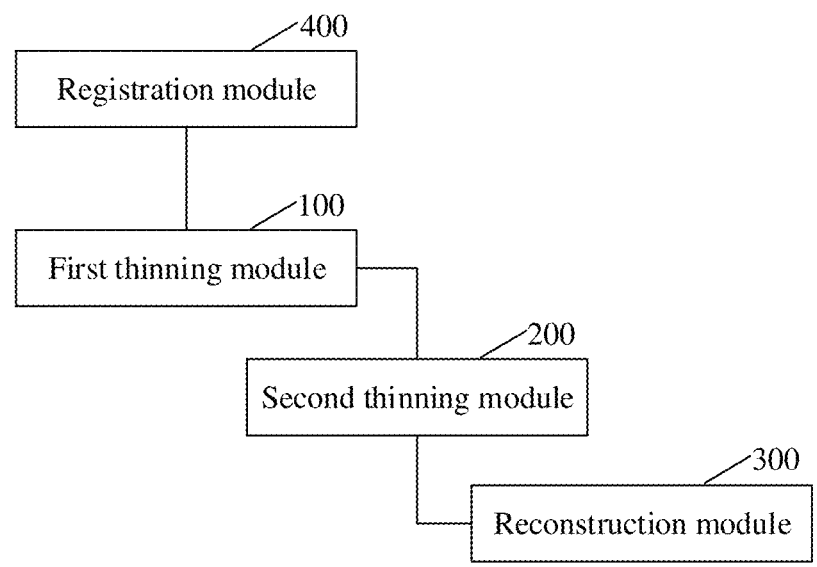
FIG. 15 is a schematic structural diagram of a super-resolution reconstruction apparatus for three-dimensional contrast-enhanced ultrasound images according to another exemplary embodiment of the present application.

FIG. 15 is a schematic structural diagram of a super-resolution reconstruction apparatus for three-dimensional contrast-enhanced ultrasound images according to another exemplary embodiment of the present application. The embodiment of the present application is extended based on the embodiment of the present application shown in FIG. 12. Differences between the embodiment of the present application and the embodiment shown in FIG. 12 are emphatically described below, and similarities may not be described repeatedly.

As shown in FIG. 15, the super-resolution reconstruction apparatus for the three-dimensional contrast-enhanced ultrasound images according to an embodiment of the present application further includes the following module.

A registration module 400 is configured to perform a registration operation on a first three-dimensional local image sequence. The registration operation includes rigid registration operations and/or flexible registration operations.

Operations and functions of the first thinning module 100, the second thinning module 200, the reconstruction module 300, the registration module 400, and the distance information determination unit 110, the first generation unit 120, the second generation unit 130 included in the first thinning module 100, and the weight value determination unit 210, the third generation unit 220, the fourth generation unit 230 included in the second thinning module 200 in the super-resolution reconstruction apparatus for the three-dimensional contrast-enhanced ultrasound images provided in FIG. 12 to FIG. 15, may refer to the super-resolution reconstruction method for three-dimensional contrast-enhanced ultrasound images provided in FIG. 3 to FIG. 11. In order to avoid repetitions, details are not repeated here.

Figure 16:
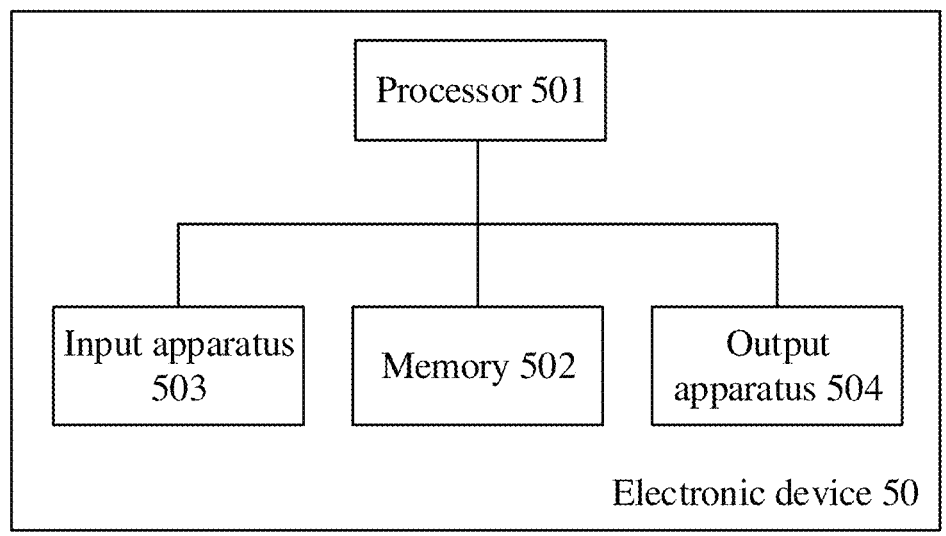
FIG. 16 is a schematic structural diagram of an electronic device according to an exemplary embodiment of the present application.

Hereinafter, an electronic device according to embodiments of the present application will be described with reference to FIG. 16. FIG. 16 is a schematic structural diagram of the electronic device according to an exemplary embodiment of the present application.

As shown in FIG. 16, the electronic device 50 includes one or more processors 501 and a memory 502.

The processor 501 may be a Central Processing Unit (CPU) or another form of processing unit with data processing capability and/or instruction execution capability, and may control another component in the electronic device to perform an expected function.

The memory 502 may include one or more computer program products, which may include various forms of computer-readable storage media, such as a volatile memory and/or non-volatile memory. The volatile memory may include, for example, a Random Access Memory (RAM) and/or a cache (cache). The non-volatile memory may include, for example, a Read-Only Memory (ROM), a hard disk, and a flash memory. The compute-readable storage medium may store one or more computer program instructions, and the processor 501 may run the super-resolution reconstruction method for three-dimensional contrast-enhanced ultrasound images and/or other expected functions of the embodiments in the present application described above. The compute-readable storage medium may further store information, such as the second three-dimensional local image sequence, or the like.

In an example, the electronic device 50 may further include an input apparatus 503 and an output apparatus 504, and these components are interconnected by using a bus system and/or another form of connection mechanism (not shown).

The input apparatus 503 may also include, for example, a keyboard, a mouse, and so on.

The output apparatus 504 may output various information including the determined three-dimensional contrast-enhanced ultrasound images to the external. The output device 504 may include, for example, a display, a communication network and a remote output device connected to it, and so on.

Certainly, for simplicity, only some of the components related to the present application in the electronic device 50 are shown in FIG. 16, and components such as a bus, and an input/output interface are omitted. In addition, the electronic device 50 may further include any other suitable component depending on specific application cases.

In addition to the foregoing methods and devices, an embodiment of the present application may also be a computer program product that includes computer program instructions. When the computer program instructions are run by a processor, the processor is enabled to perform the steps of the super-resolution reconstruction method for three-dimensional contrast-enhanced ultrasound images according to the embodiments of the present application described in the "Exemplary Methods" part of this specification.

The computer program product may write program code for performing the operations of the embodiments of the present application in any combination of one or more programming languages, and the programming languages include object-oriented programming languages such as Java and C++, and further include general procedural programming languages such as "C" or similar programming languages. The program code may be executed entirely on a user computing device, partly on a user device, as a stand-alone software package, partly on a user computing device while partly on a remote computing device, or entirely on a remote computing device or a server.

In addition, an embodiment of the present application may also be a computer-readable storage medium, where the computer-readable storage medium stores computer program instructions. When the computer program instructions are run by a processor, the processor is enabled to perform the steps of the super-resolution reconstruction method for three-dimensional contrast-enhanced ultrasound images according to the embodiments of the present application described in the "Exemplary Methods" part of this specification.

The computer-readable storage medium may use any combination of one or more readable media. The readable medium may be a readable signal medium or a readable storage medium. The readable storage medium may include, for example, but not limited to, an electronic, magnetic, optical, electromagnetic, infrared, or semiconductor system, apparatus, or means, or any combination of the above. More specific examples (a non-exhaustive list) of the readable storage medium include: an electrical connection having one or more wires, a portable computer disk, a hard disk, a Random Access Memory (RAM), a Read-Only Memory (ROM), an Erasable Programmable Read-Only Memory (EPROM or a flash memory), an optical fiber, a portable Compact Disk Read-Only Memory (CD-ROM), an optical storage means, a magnetic storage means, or any suitable combination of the above.

The foregoing describes basic principles of the present application with reference to specific embodiments. However, it may be noted that the merits, advantages, effects, and the like mentioned in the present application are merely examples but not limitations, and cannot be considered that these merits, advantages, effects, and the like are essential to the embodiments of the present application. In addition, the specific details disclosed above are intended only for the purpose of illustration and convenience of understanding, and are not limited thereto, and are not intended to limit the present application to the specific details described above.

The block diagrams of components, apparatuses, devices and systems in the present application are merely illustrative examples and are not intended to require or imply that connections, arrangements and configurations must be performed in the manner shown in the block diagrams. As will be recognized by those skilled in the art, these components, apparatuses, devices and systems can be connected, arranged and configured in any manner. Terms such as "comprise", "include", "have" are open words, meaning "include but not limited to", and they can be used interchangeably. Terms "or" and "and" used herein refer to "and/or", and they can be used interchangeably unless the context expressly indicates otherwise. Term "such as" used herein refers to "such as but not limited to" and they can be used interchangeably.

It may also be noted that, in the apparatuses, devices and methods of the present application, components or steps can be decomposed and/or recombined. These decompositions and/or recombination shall be considered as equivalent solutions of the present application.

The foregoing descriptions of the disclosed aspects are provided to enable any person skilled in the art to make or use the present application. Modifications to these aspects are very obvious to those skilled in the art and the general principles defined herein can be applied to other aspects without departing from the scope of the present application. Therefore, the present application is not intended to be limited to the aspects shown herein, but to the widest extent consistent with the principles and novel features disclosed herein.

The above description has been presented for the purposes of illustration and description. Furthermore, this description is not intended to limit the embodiments of the present application to the forms disclosed herein. Although a number of example aspects and embodiments have been discussed above, those skilled in the art will recognize certain variations, modifications, changes, additions and sub-combinations thereof.

The above are only the implementation manners of the present application, and the description is relatively specific and detailed, but it should not be understood as a limitation to the scope of the present application. It should be pointed out that for those of ordinary skill in the art, without departing from the concept of the present application, several modifications and improvements may be made, and these all fall within the protection scope of this application.

What is claimed is:

1. A super-resolution reconstruction method for three-dimensional contrast-enhanced ultrasound images, applied to a first three-dimensional local image sequence comprising microbubbles, comprising:
performing at least one thinning operation on the first three-dimensional local image sequence, wherein the thinning operation is used to enhance motion trajectories of microbubbles; and
performing an image reconstruction operation based on the first three-dimensional local image sequence subjected to the at least one thinning operation, so as to generate a three-dimensional super-resolution image;
wherein the performing at least one thinning operation on the first three-dimensional local image sequence comprises:
performing a first thinning operation on the first three-dimensional local image sequence to generate a second three-dimensional local image sequence corresponding to the first three-dimensional local image sequence, wherein the first thinning operation is used to enhance motion trajectories of microbubbles for a first time; and
performing a second thinning operation on the second three-dimensional local image sequence to generate a third three-dimensional local image sequence corresponding to the second three-dimensional local image sequence, wherein the second thinning operation is used to enhance motion trajectories of microbubbles for a second time;
wherein the performing an image reconstruction operation based on the first three-dimensional local image sequence subjected to the at least one thinning operation, so as to generate a three-dimensional super-resolution image comprises:
performing an image reconstruction operation based on the third three-dimensional local image sequence, so as to generate three-dimensional super-resolution images corresponding to the third three-dimensional local image sequence.

2. The super-resolution reconstruction method for three-dimensional contrast-enhanced ultrasound images according to claim 1, wherein the performing a first thinning operation on the first three-dimensional local image sequence to generate a second three-dimensional local image sequence corresponding to the first three-dimensional local image sequence comprises:
determining, for each frame of the first three-dimensional local image in the first three-dimensional local image sequence, distance information between a microbubble area in the first three-dimensional local image and a background area corresponding to the microbubble area;
performing a first weighting operation on the first three-dimensional local image based on the distance information to generate a first weighted image; and
generating the second three-dimensional local image sequence based on the first weighted images respectively corresponding to the first three-dimensional local images in the first three-dimensional local image sequence.

3. The super-resolution reconstruction method for three-dimensional contrast-enhanced ultrasound images according to claim 2, wherein the determining distance information between a microbubble area in the first three-dimensional local image and a background area corresponding to the microbubble area comprises:
performing binarization processing on the first three-dimensional local images based on the microbubble area and the background area to generate a binarized image; and
determining the distance information between the microbubble area and the background area based on the binarized image.

4. The super-resolution reconstruction method for three-dimensional contrast-enhanced ultrasound images according to claim 2, wherein a pixel value of a pixel coordinate corresponding to the microbubble area is set to 1, and a pixel value of a pixel coordinate corresponding to the background area is set to 0.

5. The super-resolution reconstruction method for three-dimensional contrast-enhanced ultrasound images according to claim 2, wherein the microbubble area comprises a plurality of pixel blocks, and the determining distance information between a microbubble area in the first three-dimensional local image and a background area corresponding to the microbubble area comprises:
determining a shortest distance from each the pixel block in the plurality of pixel blocks to the background area respectively; and
determining the distance information based on the shortest distances respectively corresponding to the plurality of pixel blocks.

6. The super-resolution reconstruction method for three-dimensional contrast-enhanced ultrasound images according to claim 1, wherein multiple frames of the second three-dimensional local images comprised in the second three-dimensional local image sequence are obtained by performing the first thinning operation on multiple frames of the first three-dimensional local images in the first three-dimensional local image sequence frame by frame.

7. The super-resolution reconstruction method for three-dimensional contrast-enhanced ultrasound images according to claim 1, wherein the performing a second thinning operation on the second three-dimensional local image sequence to generate a third three-dimensional local image sequence corresponding to the second three-dimensional local image sequence comprises:
performing, for each frame of the second three-dimensional local image in the second three-dimensional local image sequence, a degree of radial symmetry estimation operation on each pixel unit in the second three-dimensional local images, so as to determine a weight value corresponding to the pixel unit;
performing a second weighting operation on the second three-dimensional local images based on the weight values respectively corresponding to the pixel units in the second three-dimensional local images to generate a second weighted image; and
generating the third three-dimensional local image sequence based on the second weighted images respectively corresponding to the second three-dimensional local images in the second three-dimensional local image sequence.

8. The super-resolution reconstruction method for three-dimensional contrast-enhanced ultrasound images according to claim 7, wherein the degree of radial symmetry estimation operation is implemented based on a degree of radial symmetry calculation method in super-resolution radial fluctuations.

9. The super-resolution reconstruction method for three-dimensional contrast-enhanced ultrasound images according to claim 7, wherein a number of sampling points is 12 and a sampling radius is 1 in the degree of radial symmetry estimation operation.

10. The super-resolution reconstruction method for three-dimensional contrast-enhanced ultrasound images according to claim 1, wherein before the performing at least one thinning operation on the first three-dimensional local image sequence, the method further comprises:
performing a registration operation on the first three-dimensional local image sequence, wherein the registration operation comprises rigid registration operations and/or flexible registration operations.

11. The super-resolution reconstruction method for three-dimensional contrast-enhanced ultrasound images according to claim 10, wherein the performing a registration operation on the first three-dimensional local image sequence comprises:
performing, by using a three-dimensional Morphon multi-scale registration method, the registration operation on the first three-dimensional local image sequence.

12. The super-resolution reconstruction method for three-dimensional contrast-enhanced ultrasound images according to claim 1, wherein the performing an image reconstruction operation based on the first three-dimensional local image sequence subjected to the at least one thinning operation, so as to generate three-dimensional super-resolution images comprises:
performing an accumulation operation on the first three-dimensional local image sequence subjected to the at least one thinning operation based on image sequence information corresponding to the first three-dimensional local image sequence, so as to generate the three-dimensional super-resolution image.

13. A non-transitory computer readable storage medium, storing a computer program for executing the super-resolution reconstruction method for three-dimensional contrast-enhanced ultrasound images according to claim 1.

14. An electronic device, comprising:
a processor; and
a memory for storing executable instructions of the processor;
wherein the processor is configured to execute a super-resolution reconstruction method for three-dimensional contrast-enhanced ultrasound images, applied to a first three-dimensional local image sequence comprising microbubbles, comprising:
performing at least one thinning operation on the first three-dimensional local image sequence, wherein the thinning operation is used to enhance motion trajectories of microbubbles; and
performing an image reconstruction operation based on the first three-dimensional local image sequence subjected to the at least one thinning operation, so as to generate a three-dimensional super-resolution image;
wherein the performing at least one thinning operation on the first three-dimensional local image sequence comprises:
performing a first thinning operation on the first three-dimensional local image sequence to generate a second three-dimensional local image sequence corresponding to the first three-dimensional local image sequence, wherein the first thinning operation is used to enhance motion trajectories of microbubbles for a first time; and
performing a second thinning operation on the second three-dimensional local image sequence to generate a third three-dimensional local image sequence corresponding to the second three-dimensional local image sequence, wherein the second thinning operation is used to enhance motion trajectories of microbubbles for a second time;
wherein the performing an image reconstruction operation based on the first three-dimensional local image sequence subjected to the at least one thinning operation, so as to generate a three-dimensional super-resolution image comprises:
performing an image reconstruction operation based on the third three-dimensional local image sequence, so as to generate three-dimensional super-resolution images corresponding to the third three-dimensional local image sequence.

15. The electronic device according to claim 14, wherein the performing a first thinning operation on the first three-dimensional local image sequence to generate a second three-dimensional local image sequence corresponding to the first three-dimensional local image sequence comprises:
determining, for each frame of the first three-dimensional local image in the first three-dimensional local image sequence, distance information between a microbubble area in the first three-dimensional local image and a background area corresponding to the microbubble area;
performing a first weighting operation on the first three-dimensional local image based on the distance information to generate a first weighted image; and
generating the second three-dimensional local image sequence based on the first weighted images respectively corresponding to the first three-dimensional local images in the first three-dimensional local image sequence.

16. The electronic device according to claim 15, wherein the determining distance information between a microbubble area in the first three-dimensional local image and a background area corresponding to the microbubble area comprises:
performing binarization processing on the first three-dimensional local images based on the microbubble area and the background area to generate a binarized image; and
determining the distance information between the microbubble area and the background area based on the binarized image.

17. The electronic device according to claim 15, wherein a pixel value of a pixel coordinate corresponding to the microbubble area is set to 1, and a pixel value of a pixel coordinate corresponding to the background area is set to 0.

18. The electronic device according to claim 14, wherein multiple frames of the second three-dimensional local images comprised in the second three-dimensional local image sequence are obtained by performing the first thinning operation on multiple frames of the first three-dimensional local images in the first three-dimensional local image sequence frame by frame.

* * * * *